US012582687B2

(12) United States Patent
Gaudout et al.

(10) Patent No.: US 12,582,687 B2
(45) Date of Patent: Mar. 24, 2026

(54) COMPOSITION BASED ON *Crocus sativus* AND *Cannabis sativa*

(71) Applicant: ACTIV'INSIDE, Beychac et Caillau (FR)

(72) Inventors: David Gaudout, Carignan de Bordeaux (FR); Stéphane Rey, Montelimar (FR); Benoit Lemaire, Libourne (FR); Séverine Dubreuil, Treillieres (FR); Benjamin Moras, Floirac (FR); Mégane Bornerie, Pessac (FR); Julien Stanisiere, Bordeaux (FR); Astrid Devulpillieres, Bordeaux (FR)

(73) Assignee: ACTIV'INSIDE, Beychac Et Caillau (FR)

( * ) Notice: Subject to any disclaimer, the term of this patent is extended or adjusted under 35 U.S.C. 154(b) by 262 days.

(21) Appl. No.: 18/294,676

(22) PCT Filed: Aug. 4, 2022

(86) PCT No.: PCT/EP2022/071900
§ 371 (c)(1),
(2) Date: Feb. 2, 2024

(87) PCT Pub. No.: WO2023/012258
PCT Pub. Date: Feb. 9, 2023

(65) Prior Publication Data
US 2025/0108084 A1    Apr. 3, 2025

(30) Foreign Application Priority Data
Aug. 4, 2021    (FR) ...................................... 2108463

(51) Int. Cl.
| | |
|---|---|
| *A61K 36/00* | (2006.01) |
| *A24B 15/167* | (2020.01) |
| *A24B 15/30* | (2006.01) |
| *A61K 9/00* | (2006.01) |
| *A61K 31/00* | (2006.01) |
| *A61K 31/11* | (2006.01) |
| *A61K 36/185* | (2006.01) |
| *A61K 36/88* | (2006.01) |
| *A61K 45/06* | (2006.01) |

| | |
|---|---|
| *A61K 47/26* | (2006.01) |
| *A61K 47/46* | (2006.01) |
| *A61P 25/28* | (2006.01) |

(52) U.S. Cl.
CPC ........ *A61K 36/3482* (2024.05); *A24B 15/167* (2016.11); *A24B 15/303* (2013.01); *A61K 9/0053* (2013.01); *A61K 31/11* (2013.01); *A61K 31/658* (2023.05); *A61K 36/88* (2013.01); *A61K 45/06* (2013.01); *A61K 47/26* (2013.01); *A61K 47/46* (2013.01); *A61P 25/28* (2018.01); *A61K 2236/33* (2013.01); *A61K 2236/37* (2013.01)

(58) Field of Classification Search
CPC .................................................. A61K 36/3482
See application file for complete search history.

(56) References Cited

FOREIGN PATENT DOCUMENTS

| | | | | |
|---|---|---|---|---|
| EP | 3446678 A1 * | 2/2019 | ........... | A61K 9/2054 |
| FR | 3054443 A1 | 2/2018 | | |
| WO | WO 2018020013 | 2/2018 | | |
| WO | WO 2018173049 A1 | 9/2018 | | |
| WO | WO 2020146383 A1 | 7/2020 | | |

OTHER PUBLICATIONS

Ferber, S., et al., "Entourage Effect": Terpenes Coupled with Cannabinoids for the Treatment of Mood Disorders and Anxiety Disorders, Current Neuropharmacology, 2020; pp. 87-96, vol. 18, No. 2.
"Effects of Saffron Extract Supplementation on Mood, Well-Being, and Response to a Psychosocial Stressor in Healthy Adults: A Randomized, Double-Blind, Parallel Group, Clinical Trial".

* cited by examiner

*Primary Examiner* — Qiuwen Mi
(74) *Attorney, Agent, or Firm* — Greer, Burns & Crain, Ltd.

(57) ABSTRACT

The present invention relates to a composition comprising (i) an extract of *Crocus sativus* comprising at least safranal, and (ii) an extract of *Cannabis sativa* comprising cannabidiol (CBD) and uses thereof as a pharmaceutical product, a food supplement, a nutritional product, a cosmetic product, or a liquid suitable for electronic cigarettes.

17 Claims, 1 Drawing Sheet

COMPOSITION BASED ON *Crocus sativus* AND *Cannabis sativa*

CROSS-REFERENCE TO RELATED APPLICATIONS

This application is a U.S. National Stage Application of PCT/EP2022/071900 filed Aug. 4, 2022, claiming the benefit of priority from FR 2108463 filed Aug. 4, 2021, the entire disclosure of both applications is herein incorporated by reference.

TECHNICAL FIELD

The invention concerns a composition comprising a mixture of molecules obtained from (i) an extract of *Crocus sativus* comprising at least safranal, and (ii) an extract of *Cannabis sativa* comprising cannabidiol (CBD) or an extract of *Crocus sativus* and *Cannabis sativa* and its uses as a pharmaceutical product, food supplement, or nutritional product, cosmetic product, or liquid suitable for electronic cigarettes.

PRIOR ART

Numerous clinical studies have demonstrated the efficacy of saffron extract, in particular *Crocus sativus*, in the treatment of depression, but also in healthy populations with mood disorders due to particular physiological conditions such as menopause or premenstrual syndrome.

More recently, a randomized double-blind clinical trial demonstrated the efficacy of a saffron extract titrated to 0.2% safranal by the HPLC method, as described in patent FR 3054443, at a dose of 30 mg/day, in improving mood in healthy subjects and reducing heart rate variability induced by acute stress (Jackson, 2021).

These various studies underline the benefits of saffron and the importance of safranal for mood disorders and depression, as well as for stress and anxiety management. Yet chronic stress can cause deleterious health effects decades later, such as an increased risk of dementia (Wheelan, 2018).

Other clinical studies have also shown that saffron supplementation in healthy subjects or in patients with cognitive decline or Alzheimer's disease can improve or maintain cognitive performance compared to a placebo, or with equivalent efficacy to reference drugs (Avgerinos, 2020).

Saffron extracts known in the prior art are mostly standardized to 2% safranal by UV spectrometry according to ISO 3632-2:2010, which overestimates the safranal content by 20 to 50 times (Garcia-Rodriguez et al., 2017 *"Comparative evaluation of an ISO 3632 method and an HPLC-DAD method for safranal quantity determination in saffron"*). New extracts whose content is measured by HPLC have recently appeared on the market, such as an extract marketed by Pharmactive with a content of 0.03% (as described in WO 2017/182688), or by Activ'Inside with a content of at least 0.2% (as described in FR 3054443). Said extracts are on maltodextrin or gum arabic carriers.

However, the efficacy of these products can still be improved to combat or even prevent certain disorders such as low mood, depression, anxiety, stress and cognitive disorders. This is the objective of the invention.

SUMMARY OF THE INVENTION

In response, the invention proposes to combine a saffron extract comprising safranal with cannabidiol.

Studies in humans have demonstrated the efficacy of cannabidiol (CBD), administered alone without Tetrahydrocannabinol (THC), at a dose of 300 mg, in reducing anxiety symptoms in healthy adults under stress. Conversely, lower (100 mg) or higher (900 mg) doses had no effect (Zuardi 2017).

However, it is known that the human body possesses receptors that are highly sensitive to cannabinoids, in particular CB1 and CB2 receptors, which together with their endogenous ligands make up the "endocannabinoid system". However, it is not possible to predict with satisfactory certainty the effects of a decrease or increase in the activity of the endocannabinoid system in a given pathology.

In fact, for a given pathology, either a harmful or a positive effect of receptor activation has been demonstrated in the tissues and organs affected by the pathology. Moreover, it has been observed that levels of two endogenous CB1 and CB2 endocannabinoids (2-AG and anandamide) can vary in the same or completely opposite directions (Di Marzo, 2008).

Furthermore, it has been suggested that crocin, a molecule present in saffron, could act as a CB1 and CB2 receptor agonist (Vafaei, 2020); while another study showed that saffron induced a decrease in CB1 and CB2 receptor gene expression (Maccarone, 2016).

Thus, according to the current state of the art, it is not possible to predict the biological effects associated with administration of a cannabinoid such as CBD alone or in combination with saffron.

However, the inventors, working on saffron and hemp individually, have surprisingly observed that a mixture of molecules obtained from a *Crocus sativus* extract comprising a volatile fraction rich in terpenes, preferably at least 0.03% safranal, more preferably at least 0.2% safranal measured by HPLC and a *Cannabis sativa* extract, in a specific ratio, enables the dose of *Crocus sativus* extract and/or the dose of *Cannabis sativa* extract to be reduced very significantly compared with the doses required when *Crocus sativus* extract or *Cannabis sativa* extract is administered alone, and thus meets this need.

The inventors have also observed that the said mixture of molecules enhances the entourage effect and thus improves the stability and bioavailability of the molecules present in *Crocus sativus* and *Cannabis sativa* extracts, and consequently a better efficacy of doses lower than the individually effective doses.

Thus, the invention concerns a composition comprising a mixture of molecules including at least safranal and at least cannabidiol, preferably obtained from *Crocus sativus* extract and *Cannabis sativa* extract or *Crocus sativus* extract and *Cannabis sativa* extract, and having a specific safranal/cannabidiol ratio.

In the course of their work, the inventors identified a specific safranal/cannabidiol ratio of particular interest for improving the entourage effect and reducing cannabidiol and/or safranal doses. Preferably said safranal/cannabidiol ratio in the composition is between 0.03/1000 and 0.03/1.

Preferably, the invention relates to a composition comprising a mixture of molecules comprising at least:
- an extract of *Crocus sativus* comprising at least 0.03% safranal, by weight relative to the total weight of the dry matter of the *Crocus sativus* extract, measured by HPLC, and an extract of *Cannabis sativa* comprising at least one cannabidiol, or
- an extract obtained from *Crocus sativus* and *Cannabis sativa* comprising at least 0.03% safranal, by weight with respect to the total weight of the dry matter of the *Crocus sativus* extract, measured by HPLC, and at least one cannabidiol.

More preferably, the composition according to the invention comprises two active ingredients based respectively on *Crocus sativus* extract and *Cannabis sativa* extract, wherein:

i. the first active ingredient is an extract of *Crocus sativus* comprising at least 0.03% safranal, by weight relative to the total weight of the dry matter of the *Crocus sativus* extract, measured by HPLC, and ii. the second active ingredient is an extract of *Cannabis sativa* comprising at least one cannabidiol (CBD).

Even more preferably, the invention relates to a composition consisting of two active ingredients (i.e. without any other active ingredient) and at least one acceptable excipient, wherein:

i. the first active ingredient is an extract of *Crocus sativus* comprising safranal, preferentially at least 0.03% safranal, by weight relative to the total weight of the dry matter of the *Crocus sativus* extract, measured by HPLC, and ii. the second active ingredient is an extract of *Cannabis sativa* comprising at least one cannabidiol (CBD).

According to one variant, the composition according to the invention comprises an active ingredient based on extract of *Crocus sativus* and *Cannabis sativa* comprising safranal, preferentially at least 0.03% of safranal, by weight relative to the total weight of the dry matter of the extract of *Crocus sativus*, measured by HPLC, and cannabidiol (CBD).

Cannabidiol is one of the many cannabinoids found in hemp (*Cannabis sativa*), and is the second highest-concentration cannabinoid after tetrahydrocannabinol (THC). CBD products have become increasingly popular around the world, and more recently in France, since they are not psychotropic as THC-based products can be.

Extracts comprising CBD, in particular *Cannabis sativa* extracts, can be differentiated according to their composition, such as full spectrum CBD extracts of *Cannabis sativa*, broad spectrum CBD extracts of *Cannabis sativa*, or CBD isolate.

Preferably, the present invention relates to a composition comprising at least one *Cannabis sativa* extract such as a broad spectrum *Cannabis sativa* extract, or CBD isolate.

Finally, according to another aspect, the present composition according to the invention is intended to improve mood, and/or cognitive performance; and/or prevent and/or treat stress, and/or anxiety, and/or depression, and/or sleep disorders, and/or memory, and/or dementia, and/or cognitive decline, and/or digestive disorders, and/or joint disorders, and/or erectile disorders, and/or vision disorders, and/or disorders related to menopause or related to premenstrual syndrome in humans or animals and can be used for these effects.

Other features and advantages will emerge from the detailed description of the invention, FIGURES and examples that follow.

DETAILED DESCRIPTION OF THE INVENTION

Definition

Figure 1B:
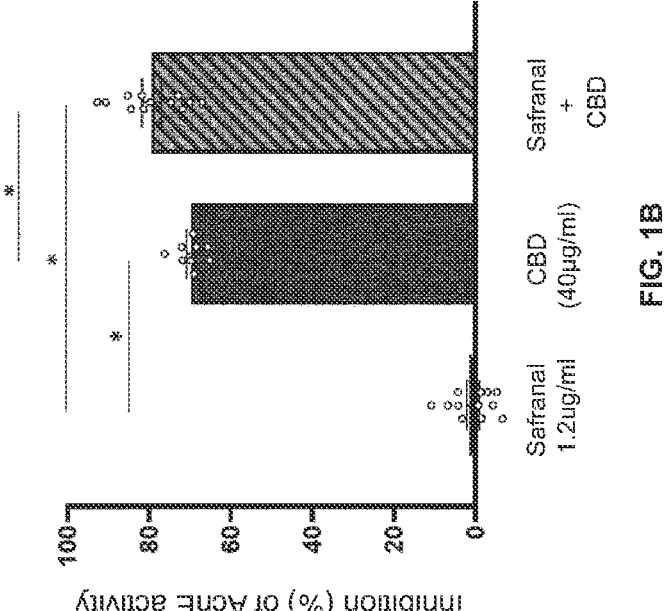
FIG. 1 represents the effect of the composition according to the invention on AChE activity. Panel A represents the slopes of the curves of normalized absorbances (mean±SEM) in their linear part, as a function of the various conditions tested. Panel B represents the percentages of inhibition (mean±SEM) of AchE activity relative to the control as a function of the various conditions tested. *$p < 0.05$

By "CBD isolate" in the sense of the invention, we mean a pure *Cannabis sativa* extract, i.e. an extract derived from *Cannabis sativa* flower, leaf, seed or stem wherein CBD is isolated from all other cannabinoids. The isolate then comprises a very high CBD content of at least 90%, preferably at least 95%, more preferably at least 98%, even more preferably at least 99%.

"Broad spectrum *Cannabis sativa* extract" or "Broad spectrum CBD extract" within the meaning of the invention means an extract of all parts (whole plant) of *Cannabis sativa*, i.e. flowers, leaves, seeds and stems, the extract comprising other cannabinoids in addition to CBD, such as cannabidol (CBN), cannabigerol (CBG) and cannabichromene (CBC), to the exclusion of tetrahydrocannabinol (THC). "Tetrahydrocannabinol exclusion" in the sense of the invention means a THC content of no more than the maximum permitted regulatory level, preferably no more than 0.2% by weight of dry matter based on the total dry matter weight of the *Cannabis sativa* extract, preferably no more than 0.1%, more preferably no more than 0%. This extract also illustrates the entourage effect.

"Cannabidol" or "CBD" in the sense of the invention means a cannabinoid present in *Cannabis sativa* extract, in particular a lipophilic bicyclic phytocannabinoid of the formula 2-[(1R,6R)-6-isopropenyl-3-methylcyclohex-2-en-1-yl]-5-pentylbenzene-1,3-diol; but also its precursor cannabidiolic acid, or cannabidiol acid (CBDA); and also CBC (cannabichromene), CBG (cannabigerol) or CBN (cannabinol). The CBDA is transformed into CBD by a decarboxylation process. Both have no psychoactive effect, but do have an entourage effect.

"Entourage effect" in the sense of the invention means the particular interaction of different terpenes, polyphenols and cannabinoids, excluding THC, which modulates the overall effects of *Cannabis sativa* on the organism.

"Total weight of the dry matter of the extract" in the sense of the invention means the dry matter is what is obtained when the water is removed from the composition or from the extract, it can be obtained by loss of the desiccation at 105° C. The dry product obtained in order to be in solid or liquid form (in the case of extracts or oily composition).

For the purposes of the invention, the term "acceptable excipient" is intended to mean any compound making it possible to facilitate the formulation of the composition and not modifying the nature of the biological activity of both active ingredients. An acceptable excipient may be a solvent, buffer, saline solution, plasticizer, lubricant, dispersion medium, absorption retarding or enhancing agent, flow agent, isotonic agent, antioxidant agent, chelating agent. For example, it may be pharmaceutically acceptable excipients that are selected according to the pharmaceutical form and the desired mode of administration, among the usual excipients known to a person skilled in the art and suitable for human and/or veterinary use. The excipient will thus be chosen according to the route of administration, e.g. suitable for oral, intravenous, intramuscular, topical etc. administration. Lastly, the excipient may be one that is acceptable in nutritional products, such as dextrins, maltodextrin, sugar, silica, glycerine, fats, vegetable waxes, hydrogenated or non-hydrogenated vegetable oils, e.g. hemp oil, proteins, peptides, alginates, phospholipids, polyols (e.g. sorbitol or maltitol), starch, cellulose, calcium or magnesium carbonate, or gum arabic.

"Extract of" in the sense of the invention means at least one molecule, preferably a set of molecules, obtained from *Crocus sativus*, or *Cannabis sativa*, or *Crocus sativus* and *Cannabis sativa*. The raw material may be the leaves and/or flowers and/or stems and/or seeds and/or stigma and/or petals, preferentially the raw material is stigma and/or petals and/or flowers of *Crocus sativus* and the flowers, leaves, seeds and stems of *Cannabis sativa*. Thus, in the context of the invention, the composition may comprise a mixture of *Crocus sativus* and *Cannabis sativa* extract or an extract derived from a mixture of *Crocus sativus* and *Cannabis sativa*.

"Safranal/cannabidiol ratio" in the sense of the invention means the ratio of the amount of safranal contained in the composition to the amount of cannabidiol contained in the composition, in particular the ratio is between 0.03/1000 and 0.03. For the purposes of the invention, the term "ratio of 0.03" refers to a ratio of 0.03 plus or minus 0.05.

"Prevention" in the sense of the invention means the reduction to a lesser degree of the risk or of the probability of occurrence of a given phenomenon, for example low mood, depression, stress or anxiety.

"Treatment" in the sense of the invention means a decrease in disease progression, stabilization, inversion or regression, or even interruption or inhibition of the progression of depression, sleep disorders, dementia, digestive disorders, joint disorders, erectile disorders, vision disorders or disorders related to menopause or related to pre-menstrual syndrome. In the context of the invention, these terms also apply to one or more symptoms of said diseases of the present invention.

Composition

The present invention therefore relates to a composition comprising a mixture of molecules comprising at least:

an extract of *Crocus sativus* comprising at least safranal, preferentially at least 0.03% safranal, by weight relative to the total weight of the dry matter of the *Crocus sativus* extract, measured by HPLC, and an extract of *Cannabis sativa* comprising at least one cannabidiol, or an extract obtained from *Crocus sativus* and *Cannabis sativa* comprising at least safranal, preferentially at least 0.03% safranal, by weight with respect to the total weight of the dry matter of the *Crocus sativus* extract, measured by HPLC, and at least one cannabidiol.

said composition having a safranal/cannabidiol ratio of between 0.03/1000 and 0.03.

In particular, the composition comprises two active ingredients, wherein:

a. the first active ingredient is an extract of *Crocus sativus* comprising at least safranal, preferentially at least 0.03% safranal, by weight relative to the total weight of the dry matter of the *Crocus sativus* extract, measured by HPLC, and b. the second active ingredient is an extract of *Cannabis sativa* comprising at least one cannabidiol (CBD).

According to a preferred variant, the composition consists of two active ingredients (i.e. without any other active ingredient) and at least one acceptable excipient, wherein:

a. the first active ingredient is an extract of *Crocus sativus* comprising at least safranal, preferentially at least 0.03% safranal, by weight relative to the total weight of the dry matter of the *Crocus sativus* extract, measured by HPLC, and b. the second active ingredient is an extract of *Cannabis sativa* comprising at least one cannabidiol (CBD).

*Crocus sativus* extract is preferably obtained from *Crocus sativus* stigma and/or petals and/or flowers comprising safranal, in particular at least 0.03%, preferably at least 0.05%, more preferably at least 0.1%, even more preferably at least 0.2% safranal by weight relative to the total weight of the dry matter, said concentration being measured by the HPLC method.

*Crocus sativus* extract may also preferably comprise other molecules such as:

at least 2% crocin by weight based on the total dry weight of the *Crocus sativus* extract, measured by HPLC and potentially considered as the sum of trans-crocin-4 (majority crocin), trans-crocin-3, trans-crocin-2', cis-crocin-4, trans crocin-2, and trans-crocin-1, and/or flavonoids derived from kaempferol and/or picrocrocin derivatives and/or terpenes, excluding safranal.

Flavonoids derived from kaempferol preferably represent at least 500 ppm by weight of dry matter in the extract, measured by the HPLC method.

Picrocrocine derivatives preferably represent at least 0.5% by weight of the extract's dry matter, measured by HPLC.

Terpenes, excluding safranal, preferably represent at least 0.03% by weight of the extract's dry matter, measured by HPLC.

"Saffron extract" within the meaning of the invention means an extract obtained from stigma and/or petals and/or flowers of the invention *Crocus sativus*, in particular at least one molecule or a set of a plurality of molecules derived from stigma and/or petals and/or flowers comprising safranal. This may involve a specific selection of native molecules present in the plant, or molecules obtained by any type of transformation of said native molecules. The raw material used to obtain the extract is the stigma and/or petals and/or flowers of *Crocus sativus*.

Preferentially, the extract of *Crocus sativus* of the composition according to the invention is encapsulated either in an aqueous phase or in a fatty phase (for example vegetable oil).

According to one preferred embodiment, the extract of *Crocus sativus* has also undergone a heat treatment after its encapsulation lasting at least 2 hours at a temperature of between 30° C. and 95° C.

When *Crocus sativus* extract is only encapsulated, the agent for encapsulating the extract is chosen from gum arabic, cyclodextrins or fats, vegetable waxes, hydrogenated or non-hydrogenated vegetable oils, oil, preferably hemp oil, proteins, peptides, dextrins, alginates, phospholipids.

According to one variant, the *Crocus sativus* extract has been obtained by a method which comprises a step consisting of simultaneously impregnating and encapsulating the *Crocus sativus* extract in the extraction solution and in a carrier selected from dextrins, maltodextrin, sugars, silica, gum arabic, glycerine, fats, vegetable waxes, hydrogenated or non-hydrogenated vegetable oils such as hemp oil, proteins, peptides, dextrins, alginates, phospholipids, more preferably maltodextrin. Said extract also preferentially undergoes a heat treatment after impregnation and encapsulation lasting at least 2 hours at a temperature of between 30° C. and 95° C.

When the extract is impregnated on a carrier, the percentages of molecules present in the extract are given by weight of dry matter of the extract including the carrier.

More preferably, the *Crocus sativus* extract is an extract obtained according to the method described in patent FR 3054443, incorporated by reference.

Thus, the extract is obtained by implementing the following steps carried out from raw material of *Crocus sativus:*

Possibly drying,

Grinding, preferably between 50 and 500 μm,

Aqueous or hydroalcoholic extraction or with an organic solvent or fatty phase, preferably vegetable oil, Impregnation and/or encapsulation of the extract obtained in the extraction solution on a support, Heat treatment, preferably for at least 2 hours at a temperature of between 30° C. and 95° C.

The heat treatment step can optionally be carried out at any point in this method, such as:

Between the drying and grinding steps, or

Between the grinding and extraction steps, or

Between extraction and the impregnation and encapsulation step, or

Preferably after the impregnation and encapsulation step.

According to one particularly suitable embodiment, the heat treatment step in the implementation of this method is a heat treatment step in an oven or a tank for at least 2 hours, even more preferentially for at least 24 hours at a temperature of between 30° C. and 95° C., even more preferentially at a temperature of between 30° C. and 60° C.

The grinding can be carried out by any known suitable means, in particular by a knife, pin or hammer mill, preferentially a pin mill.

The extraction step can be carried out by any known suitable means. In the case of an aqueous extraction, the ground material is introduced into the water at 50 g/L.

In the case of hydroalcoholic extraction, the solvent may be ethanol, preferably 60% v/v ethanol. The ground material is introduced into the hydroalcoholic solution at a rate of 50 g/L.

In the case of extraction with an organic solvent, the solvent may in particular be methanol or ethyl acetate, preferentially 30% v/v methanol. The ground material is introduced into the organic solvent at a rate of 100 g/L.

After extraction, the method may also comprise an acidification step. This step consists of adding acid to the aqueous or hydroalcoholic solvent. It reduces the pH of the extraction solution between 3 and 5. This can be achieved by adding citric acid or hydrochloric acid to the hydroalcoholic solvent to adjust the pH to 4.

In the case of extraction with a fatty phase, the fatty phase can be olive oil, hemp oil, coconut oil, sunflower oil or rapeseed oil. The solution can be heated to at least 60° C. According to a preferred embodiment, such extraction can make it possible to obtain an extract of *Crocus sativus* and *Cannabis sativa.*

The step of impregnation and encapsulation simultaneously on the carder consists of adding a filler into the extraction solution, i.e. in the liquid state. More preferably, such a step is also carried out simultaneously with the extraction step, enabling the safranal and crocin molecules to be trapped during extraction. The trapping of safranal molecules results in an extract with a high safranal concentration of at least 0.2%, as measured by HPLC, and encapsulation for improved stability of both safranal and crocin.

The carrier or filler or excipient may be selected from the following constituents: maltodextrin, sugar, silica, gum arabic, cyclodextrins or fats, vegetable waxes, hydrogenated or non-hydrogenated vegetable oils, such as hemp oil, proteins, peptides, dextrins, alginates, phospholipids, preferably maltodextrin. Antioxidants and/or chelating agents may be added to allow better stability of the molecules of interest. This step consists of high-speed agitation of the extraction solution containing the excipient or carrier filler.

A double emulsion can also be envisaged with surfactants known to the art to enable solubilization in water of the initially encapsulated or microencapsulated extract, thus constituting a double encapsulation or microencapsulation. Microencapsulation makes it possible to protect the active substances within particles having sizes of between 1 μm and 1000 μm, preferentially between 1 μm and 500 μm, more preferentially between 5 μm and 100 μm, even more preferentially between 5 μm and 50 μm.

The molecules derived from the second active principle present in the composition according to the invention is obtained from hemp, in particular from *Cannabis sativa.* The latter contains different metabolites of interest, which can be classified into three large families: cannabinoids (called "phytocannabinoids"), terpenes and polyphenols.

Cannabinoids of *Cannabis sativa* include in particular THC and CBD and will act on CB1 and CB2 receptors. CB1 is mostly localized at the central nervous system and peripheral nerve terminations, whereas CB2 is essentially found in the immune system cells and the spleen.

THC is the component originally of the psychotropic effects of *cannabis*, conferring euphoria and relaxing effects. However, the consumption of THC also induces an alteration of cognitive functions. Unlike THC, CBD does not have psychotropic effects despite well-being such as reducing stress, expansion, or improving sleep. It also helps to support certain chronic pain. In addition, CBD, consumed before THC, is said to be able to attenuate the euphoric effects of THC, but also to counteract its deleterious effects, such as impaired psychomotor performance, anxiety and psychosis.

Preferably, the *Cannabis sativa* extract according to the invention is a broad-spectrum *Cannabis sativa* extract or a CBD isolate.

Thus, it comprises no THC, i.e. the amount of THC present in said extract is at most the maximum regulatory content allowed, preferably at most 0.2%, most preferably at most 0%.

Preferably, the *Cannabis sativa* extract according to the invention comprises at least 90% cannabidiol or between 0.1% and 50% cannabidiol, more preferably between 0.1% and 10% cannabidiol expressed by weight relative to the total weight of the dry matter of the *Cannabis sativa* extract.

*Cannabis sativa* extract also contains terpenes.

Among the terpenes present in the majority of *Cannabis sativa* varieties are the monoterpene myrcene (hereinafter referred to as myrcene) and the sesquiterpenes β-caryophyllene and α-humulene. The α-pinene monoterpenes, limonene and linalool, as well as sesquiterpene bisabolol, are also common terpenes. Said *Cannabis sativa* extract does not comprise any safranal.

Preferably, the *Cannabis sativa* extract comprises at least 0.001% terpenes, by weight relative to the total weight of the dry matter of the *Cannabis sativa* extract, more preferably at least 0.01% terpenes, even more preferably at least 0.05% terpenes.

According to a particularly preferred embodiment, it comprises between 0.1% and 10% of cannabidiol and at least 0.001% of terpenes by weight relative to the total weight of the dry matter of the extract of *Cannabis sativa*, more preferably at least 0.01% terpenes, even more preferably at least 0.05% terpenes.

Among the multitude of terpenes present in *Cannabis sativa*, the *Cannabis sativa* extract present in the composition according to the invention comprises myrcene, which preferably represents at least 5 ppm, more preferably at least 100 ppm, by weight relative to the total weight of the dry matter of the *Cannabis sativa* extract.

In addition, the terpenes predominantly present in *Cannabis sativa* species are not found in *Crocus sativus* species, in particular myrcene is not present in *Crocus sativus* extract, which is present in the composition according to the invention.

The last metabolites of interest present in *Cannabis sativa* are polyphenols. Hemp contains around twenty different flavonoids, some of which are specific to it, such as cannflavins A and B (known for their anti-inflammatory properties). Quercetins, kaempferol, catechins and luteolin are also known for their nootropic properties. The polyphenols present in *Cannabis sativa* also contribute, along with cannabinoids and terpenes, to the entourage effect.

To obtain the composition according to the invention, *Crocus sativus* extract is mixed with *Cannabis sativa* extract and optionally at least one excipient, or the extract is derived from a mixture of *Crocus sativus* and *Cannabis sativa* and optionally at least one excipient.

According to a particularly interesting and preferred object, the safranal/cannabidiol ratio in the composition is between 0.03/100 and 0.03, more preferably is between 0.03/25 and 0.03. Such a ratio further enhances the synergistic effects observed between *Crocus sativus* extract comprising at least 0.2% safranal, as measured by HPLC, and *Cannabis sativa* extract. In particular, it enables an improved entourage effect to be obtained, which means that the dose of CBD and/or the dose of *Crocus sativus* extract, in particular safranal, can be significantly reduced compared with the doses required when CBD or *Crocus sativus* extract is administered alone.

More preferably, the composition according to the invention has a safranal/myrcene ratio greater than 0.03, preferably greater than 0.1, more preferably greater than 1.

The composition according to the invention can be prepared by implementing the following steps:

a. preparing the *Crocus sativus* extract as described above,
b. preparing the *Cannabis sativa* extract as described above,
c. mixing the two extracts,
d. adding an antioxidant agent,
e. optionally, a step of encapsulating the two active ingredients and the antioxidant agent.

According to one variant, the composition according to the invention can be prepared by implementing the following steps:

a. preparing the extract of *Crocus sativus* and *Cannabis sativa* simultaneously,
b. adding an antioxidant agent,
c. optionally, a step of encapsulating said extract and the antioxidant.

The composition according to the invention may also comprise an antioxidant and/or chelating agent selected from the following substances: ascorbic acid E300, α-tocopherol (vitamin E E306), E309, rosemary extract E392, *Crocus sativus* extract (and more particularly petals) containing flavonols, and more particularly kaempferols, BHA E320, BHT E321, E330 and citric acid or EDTA or proteins as chelating agents. The proteins are preferably selected from protein extracts of rice bran, hydrolyzed wheat germ, barley bran, oat bran, soy protein hydrolysate as described by Mallory E Walters et al. 2018 "Potential of Food Hydrolyzed Proteins and Peptides to Chelate Iron or Calcium and Enhance their Absorption". The antioxidant and/or chelating agent thus stabilizes and preserves the safranal, crocins, CBD, terpenes and polyphenols present in the composition over time, thereby maintaining the associated biological effects, including synergistic effects in combination.

Preferably, the antioxidant is present in the composition according to the invention so that the ratio of antioxidant to safranal is from 1/100 to 10/1, by weight of safranal dry matter, measured by HPLC analysis.

The antioxidant and/or chelating agent preferably represents 0.01 g/100 g of crocin to 25 g/100 g by weight of crocin dry matter, measured by the HPLC method.

For example, the antioxidant vitamin may be vitamin C and/or vitamin E.

By way of example, the polyphenols derived from *Crocus sativus* and/or *Cannabis sativa* extract may be flavonoids such as cannflavins A and B, quercetin, kaempferol, catechins and/or luteonin.

The composition according to the invention may be in a dry, liquid or gel form.

Preferably, the composition according to the invention is in the form of a liquid, an oily liquid, an electronic cigarette liquid, a powder, a soft capsule, a gelcap, a tablet, a stick, a sachet, gummies, a cream, a lotion, an oil, a gel, a transdermal patch, a prepared dish, or a drink.

The composition according to the invention may optionally comprise other known suitable components, such as excipients, selected as a function of the envisaged form and use of the composition.

According to a preferred object, the composition comprises at least 15 mg of *Crocus sativus* extract and at least 3 mg of CBD. Preferably, said composition is administered on a per-day or per-dose basis to a human being.

Said composition can be administered for example in one or two doses.

The composition can be used in numerous applications. Thus, the object of the invention is a composition according to the invention for use in the treatment or prevention of at least one disorder selected from depression, anxiety, stress, mood disorders (including pathological mood disorders), memory disorders, erectile disorders, menopausal or premenstrual syndrome disorders, sleep disorders, digestive disorders, joint disorders, vision disorders, dementia, cognitive decline (including pathological disorders of cognitive decline), and combinations thereof in humans or animals.

The composition may also improve the non-pathological mood, and/or cognitive performance, and/or memory and/or non-pathological cognitive decline linked to age in human or animal.

The invention is now illustrated by non-limiting examples of compositions according to the invention.

EXAMPLES

Example 1—Composition According to the Invention

A first example of a composition according to the invention is obtained by implementing the method consisting of the implementation of the following steps:

a. Obtaining an extract of *Crocus sativus* according to the method described in patent FR 3054443
b. Obtaining an extract of *Cannabis sativa* by implementing the following steps:
an extraction process using organic solvents such as ethanol or a hydroalcoholic mixture as described in Glivar et al., 2020 or using supercritical $CO_2$ as described in Nogueira et al., 2018 or, due to its lipophilic nature, using a preferably vegetable oil such as olive oil as described in Casiraghi et al., 2018.

decarboxylation of CBDA by applying a thermal method during or after extraction, at temperatures of 100 to 140° C. (the thermal method to decarboxylate CBDA can also be applied to the raw material, prior to extraction). Oil extraction can also involve decarboxylation by heating the oil to a temperature of at least 110° C. for a minimum of 40 min.

c. Mixing the *Crocus sativus* and *Cannabis sativa* extracts obtained in steps a and b respectively.

The composition then comprises the following characteristics, for a daily dose:

15 mg of *Crocus sativus* extract titrated to 0.2% safranal measured by HPLC, equivalent to 0.03 mg safranal, 10 mg of *Cannabis sativa* extract titrated to 10% CBD and 0.2% myrcene, equivalent to 1 mg CBD and 0.02 mg myrcene.

Example 2—Composition According to the Invention

A second example of a composition according to the invention is obtained by implementing the method consisting of the implementation of the following steps:

a. simultaneously extracting and heating, in a fatty substance, *Crocus sativus* and *Cannabis sativa* to a minimum temperature of 80° C., b. obtaining an extract from the mixture of *Crocus sativus* and *Cannabis sativa*.

The composition then comprises the following characteristics:

10 mg of saffron titrated to 0.03% of safranal measured by HPLC, i.e. the equivalent of 0.003 mg of safranal 26.3 mg of *Cannabis sativa* isolate titrated to 95% CBD and 0.038% myrcene, equivalent to 25 mg CBD and 0.01 mg myrcene.

0.03 μg of rosemary extract.

Example 3—Composition According to the Invention

A third example of a composition according to the invention is obtained by implementing one of the methods described in examples 1 and 2.

The composition then comprises the following characteristics:

10 mg of a *Crocus sativus* extract titrated to 0.2% safranal measured by HPLC, equivalent to 0.02 mg safranal, 26.3 mg of a *Cannabis sativa* isolate titrated to 95% CBD and 0.038% myrcene, equivalent to 25 mg CBD and 0.01 mg myrcene.

0.3 μg of rosemary extract.

Example 4—Composition According to the Invention

A fourth example of a composition according to the invention is obtained by implementing one of the methods described in examples 1 and 2.

The composition then comprises the following characteristics:

10 mg of a *Crocus sativus* extract titrated to 0.2% safranal measured by HPLC, equivalent to 0.02 mg safranal, 150 mg of a *Cannabis sativa* isolate titrated to 10% CBD and 0.32% myrcene, equivalent to 15 mg CBD and 0.48 mg myrcene.

15 μg vitamin E (α-tocopherol)

Example 5—Composition According to the Invention

A fifth example of a composition according to the invention is obtained by implementing one of the methods described in examples 1 and 2.

The composition then comprises the following characteristics:

10 mg of a *Crocus sativus* extract titrated to 0.2% safranal measured by HPLC, equivalent to 0.02 mg safranal, 20.2 mg of a *Cannabis sativa* isolate titrated to 99% CBD, equivalent to 20 mg CBD.

3 μg vitamin E (α-tocopherol)

Example 6—Nutritional Composition According to the Invention

A sixth example of a composition according to the invention is obtained by incorporating the composition according to example 1 in a chocolate cookie recipe, consumed by a person at a rate of 2 cookies per day.

Said recipe consists, for 10 cookies, of:

200 g flour 10 g baking powder 40 g coconut powder 125 g chocolate chips (dark or milk chocolate, to taste)

80 g sugar 1 egg 120 g butter

Example 7—Liquid Composition for an Electronic Cigarette According to the Invention A seventh example of a composition according to the invention is obtained by incorporating the composition according to example 1 in a liquid formula for an electronic cigarette intended for humans at a rate of 2 mL of liquid per day.

Said liquid formula for an electronic cigarette consists, for 1 vial of 10 ml, of:

8 mL propylene glycol, 1 mL vegetable glycerine 0.5 g food flavoring 100 mg nicotine Ethanol and/or demineralized water: qs 10 ml.

Example 8—Liquid Composition for an Electronic Cigarette According to the Invention An eighth example of a composition according to the invention is obtained by incorporating the composition according to example 1 in a liquid formula for an electronic cigarette intended for humans at a rate of 2 mL of liquid per day.

Said liquid formula for an electronic cigarette consists, for 1 vial of 10 ml, of:

8 mL propylene glycol, 1 mL vegetable glycerine 0.5 g food flavoring

Ethanol and/or demineralized water: qs 10 ml.

Efficacy Assessment of the Composition According to the Invention

Test 1: Assessment of the Effect of the Composition According to the Invention on Acetylcholinesterase Activity.

Acetylcholine is a neurotransmitter that plays a major role in memory and recall. In neurodegenerative processes such as dementia, acetylcholine levels are reduced, which explains the appearance of cognitive and psychobehavioral symptoms. One of the objectives of the current treatments is to maintain normal acetylcholinergic neurotransmission by inhibiting its degradation, namely by inhibiting the activity of acetylcholinesterase (the enzyme responsible for the degradation of acetylcholine).

The aim of this assay is to compare acetylcholinesterase (AchE) activity in the presence of the composition according to the invention, with a safranal/cannabidiol (CBD) ratio of 0.03, with acetylcholinesterase activity in the presence of safranal or CBD alone.

AchE activity was monitored and measured in vitro by colorimetric reaction using the Ellman method. Acetylthiocholine (ATCl) is degraded to thiocholine and acetic acid by AChE. The thiocholine then reacts with the dithiobisnitrobenzoic ion (DTNB) and the resulting ion (TNB) gives a yellow coloration. In a 96-well plate, the following amounts were deposited in each well: 55 µl buffer (Tris-HCl 50 mM), 75 µl DTNB (5 mM), 25 µl AchE (0.22 U/ml), 25 µl test sample (buffer or safranal (1.2 µg/ml), or CBD (40 µg/ml), or safranal (1.2 µg/ml)+CBD (40 µg/ml).

At the last moment, 25 µL of ATCl (1 mM) was added to initiate the reaction. The absorbance was then monitored at 405 nM for 20 min. The results were analyzed as follows. For each well, the absorbance values over time (Ax) are normalized relative to the first absorbance measurement ($A_{T0}$) according to the following formula: Normalized absorbance ($A_n$)=$A_x$–$A_{T0}$. The percentage of AchE inhibition was determined by comparing the slopes of the curves (in the linear part) against the control according to the following equation [Math 1].

$$\% \text{ inhibition} = \frac{\text{Slope}_{(Control)} - \text{Slope}_{(sample)}}{\text{Slope}_{(sample)}} \times 100 \qquad \text{[Math 1]}$$

The values of the slopes and of the percentages of inhibition were statistically compared using analysis of variance (ANOVA). A value of $p<0.05$ is considered significant.

Figure 1A:
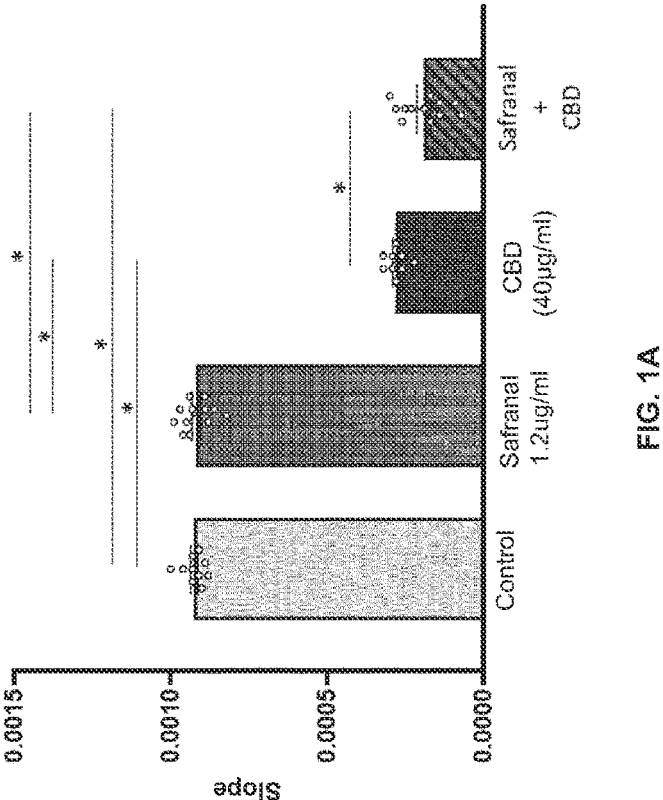

The results show that in the presence of safranal, AchE activity is unchanged compared with the control (FIG. 1). On the other hand, in the presence of CBD, a significant decrease (69.8%) in AchE activity was observed. Finally, in the presence of the composition according to the invention, inhibition of acetylcholinesterase activity is significantly greater than in the presence of CBD alone (79.4% vs. 69.8%). Such results demonstrate the presence of synergistic interactions between safranal and CBD on AchE activity, enabling its activity to be more significantly reduced. The reduction in its activity by the composition according to the invention thus makes it possible to improve cholinergic transmission and consequently cognitive functions.

The invention claimed is:

1. A composition comprising a mixture of molecules comprising at least:
   an extract of *Crocus sativus* comprising at least safranal, and an extract of *Cannabis sativa* comprising at least one cannabidiol, or
   an extract obtained from *Crocus sativus* and from *Cannabis sativa* comprising at least safranal and at least one cannabidiol,

said *Cannabis sativa* extract comprising at most 0.2% Tetrahydrocannabinol (THC) by weight of dry matter based on the total weight of dry matter of the *Cannabis sativa* extract,
said composition comprising a safranal/cannabidiol ratio of between 0.03/1000 and 0.03.

2. The composition according to claim 1, characterized in that the *Crocus sativus* extract or the extract obtained from *Crocus sativus* and from *Cannabis sativa* comprises at least 0.03% safranal, by weight relative to the total weight of the dry matter of the *Crocus sativus* extract, measured by HPLC.

3. The composition according to claim 1, characterized in that the *Cannabis sativa* extract is a broad-spectrum *Cannabis sativa* extract or a CBD isolate.

4. The composition according to claim 1, characterized in that it the *Cannabis sativa* extract comprises:
   between 0.1% and 10% cannabidiol, expressed by weight relative to the total dry weight of the *Cannabis sativa* extract, or
   at least 90% cannabidiol, expressed by weight relative to the total weight of the dry matter of the *Cannabis sativa* extract.

5. The composition according to claim 4, characterized in that the *Cannabis sativa* extract comprises between 0.1% and 10% cannabidiol and at least 0.001% terpenes, by weight relative to the total weight of the dry matter of the *Cannabis sativa* extract.

6. The composition according to claim 5, characterized in that the terpenes represent at least 0.01% by weight relative to the total weight of the dry matter of the *Cannabis sativa* extract.

7. The composition according to claim 6, characterized in that the terpenes comprise at least myrcenes.

8. The composition according to claim 1, characterized in that the *Crocus sativus* extract is an extract of stigma and/or petals and/or flowers of *Crocus sativus*.

9. The composition according to claim 1, characterized in that it the *Crocus sativus* extract comprises:
   at least 2% of crocins by weight relative to the total weight of the dry matter of the *Crocus sativus* extract, measured by the HPLC method;
   flavonoids derived from kaempferol and/or picrocrocin derivatives and/or terpenes, excluding safranal.

10. The composition according to claim 1, characterized in that the *Crocus sativus* extract is encapsulated with an agent selected from gum arabic, cyclodextrins, fats, vegetable waxes, hydrogenated or non-hydrogenated vegetable oils, hemp oil, proteins, peptides, dextrins, alginates, phospholipids.

11. The composition according to claim 1, characterized in that the extract of *Crocus sativus* is obtainable by a process comprising an aqueous or hydroalcoholic extraction or with an organic solvent or a fatty phase, a step of encapsulating the extract with an agent in the extraction solution and a step of heat treatment lasting at least 2 hours at a temperature of between 30° C. and 95° C.

12. The composition according to claim 1, characterized in that the safranal/cannabidiol ratio is between 0.03/100 and 0.03.

13. The composition according to claim 1, characterized in that the composition also comprises an antioxidant agent.

14. The composition according to claim 1, characterized in that the composition comprises at least 15 mg *Crocus sativus* extract and at least 3 mg CBD.

15. The composition according to claim 1, characterized in that the composition is in dry, liquid or gel form.

16. The composition according to claim 15, characterized in that it is in the form of a liquid, oily liquid, e-cigarette liquid, powder, soft capsule, gelcap, tablet, stick, sachet, chewing gum, cream, lotion, oil, gel, transdermal patch, prepared dish or beverage.

17. The composition according to claim 1 for use in improving mood, and/or cognitive performance; and/or preventing and/or treating stress, and/or anxiety, and/or depression, and/or sleep disorders, and/or memory, and/or dementia, and/or cognitive decline, and/or digestive disorders, and/or joint disorders, and/or erectile disorders, and/or vision disorders, and/or disorders related to menopause or premenstrual syndrome in humans or animals.

\* \* \* \* \*